United States Patent [19]
Lazarus

[11] Patent Number: 5,871,536
[45] Date of Patent: *Feb. 16, 1999

[54] INTRALUMINAL VASCULAR GRAFT AND METHOD

[76] Inventor: Harrison M. Lazarus, 853 Thirteenth Ave., Salt Lake City, Utah 84103

[ * ] Notice: This patent issued on a continued prosecution application filed under 37 CFR 1.53(d), and is subject to the twenty year patent term provisions of 35 U.S.C. 154(a)(2).

[21] Appl. No.: 568,559

[22] Filed: Dec. 7, 1995

Related U.S. Application Data

[63] Continuation of Ser. No. 149,040, Nov. 8, 1993, abandoned.

[51] Int. Cl.$^6$ .......................................................... A61F 2/06
[52] U.S. Cl. .................................................. 623/1; 623/12
[58] Field of Search ............................... 600/36; 606/157, 606/158, 153, 198, 194, 195; 623/1, 11, 12

[56] References Cited

U.S. PATENT DOCUMENTS

| | | |
|---|---|---|
| 4,140,126 | 2/1979 | Choudhury ............................... 604/175 |
| 4,355,426 | 10/1982 | MacGregor ................................. 623/1 |
| 4,562,596 | 1/1986 | Kornberg . | 
| 4,577,631 | 3/1986 | Kreamer . |
| 4,617,932 | 10/1986 | Kornberg .................................... 623/1 |
| 5,104,399 | 4/1992 | Lazarus . |
| 5,123,917 | 6/1992 | Lee . |
| 5,151,105 | 9/1992 | Kwan-Gett .................................. 623/1 |
| 5,290,305 | 3/1994 | Inoue .......................................... 623/1 |
| 5,330,500 | 7/1994 | Song .......................................... 623/1 |

*Primary Examiner*—Debra S. Brittingham
*Attorney, Agent, or Firm*—Trask, Britt & Rossa

[57] ABSTRACT

An intraluminal vascular graft structure is disclosed which is structured to be deployable within a vessel without use of hooks or barbs. The intraluminal vascular graft structure comprises a tubular body formed of a biocompatible material and a frame structure, having both circumferential support and longitudinal support structures, which support the graft at a distal end thereof and upwardly from the distal end. The vascular graft may also include attachment means which initiate an inflammatory response with the inner wall of the vessel to promote attachment of the device to the vessel wall. The intraluminal vascular graft may include one or more leg portions suitable for repairing bifurcated vessels which, in conjunction with the circumferential and longitudinal support structures, assure positioning and support of the vascular graft within the vessel and against the crotch of the bifurcation. Also disclosed is a method of deployment of the vascular graft within the vessel.

33 Claims, 5 Drawing Sheets

INTRALUMINAL VASCULAR GRAFT AND METHOD

This application is a continuation of application Ser. No. 08/149,040, filed Nov. 8, 1993, now abandoned.

BACKGROUND OF THE INVENTION

1. Technical Field

This invention relates to medical devices in general, and specifically to grafts positionable intraluminally for repairing aneurysms or other vascular defects in humans and animals.

2. Background

Aneurysms are caused by weakening of a vessel wall which results in the outward ballooning of the wall under the pressure of flowing blood. Aneurysms are more prevalent in men than in women, and are more common with advancing age. Prior to the development of technology to repair the bulging blood vessel, aneurysms posed a fatal threat to those who developed them. Even with the early development of repair procedures, significantly invasive surgery was required to access the aneurysm. Today, graft structures have been developed which allow insertion and delivery of the graft to the point of the aneurysm using less invasive procedures.

Known intraluminal graft structures generally comprise a tubular graft, expansion means for deploying and positioning the graft in the vessel and anchoring or attachment means for keeping the graft in place within the vessel. Many varying types of expansion means have been disclosed, including those described in U.S. Pat. No. 4,140,126 to Choudhury (expandable ring positioned at open end of graft); U.S. Pat. No. 4,776,337 to Palmaz (a mesh-like tube); U.S. Pat. No. 5,123,917 to Lee (zig-zagged expandable ring); and U.S. Pat. No. 5,151,105 to Kwan-Gett (helically-coiled spring). Means have also been described for providing longitudinal support to the graft, including those means described in U.S. Pat. No. 4,562,596 to Kornberg (a plurality of steel struts) and U.S. Pat. No. 5,151,105 to Kwan-Gett (diametrically spaced adjustable ribs).

Additionally, various means for attaching the graft to the vessel have been disclosed. Most frequently, hook, barb or pin means are described and used, including the means described in U.S. Pat. No. 4,140,126 to Choudhury (a plurality of pins); U.S. Pat. No. 4,562,596 to Kornberg (a plurality of barbs; and U.S. Pat. No. 5,151,105 to Kwan-Gett (staples). In some instances, the hook or barb means are attached to the expandable means as described in U.S. Pat. No. 4,140,126 to Choudhury and U.S. Pat. No. 5,104,399 to Lazarus. U.S. Pat. No. 4,577,631 to Kreamer discloses use of an adhesive covering the entire outside of the graft to provide adherence of the luminal intima to the graft.

The most commonly used intraluminal graft structures have hooks or barbs which pierce into or through the wall of the vessel to anchor the graft to the vessel above the aneurysm. That is, most, if not all, currently used intraluminal grafts are supported in the vessel upstream from or above the disease condition. However, hooks or barbs may damage the vessel, particularly where the vessel is weakened already by an aneurysm or other disease condition. Additionally, there are instances when the condition of the vessel may make it impossible or imprudent to use a graft device having hooks or pins, such as the existence of calcium deposits. Such conditions may also limit the usefulness of adhesives.

Thus, it would be advantageous to provide an intraluminal graft which is adapted for use in vascular repair under any conditions, but particularly under conditions which limit or prevent the use of intraluminal grafts having hook, pin, barb or staple attachment means. That is, it would be advantageous to provide an intraluminal graft which is structured to be supportable from a position downstream or below the disease condition to thereby eliminate the need for hook, pin, barb or staple anchoring means. Such structure would allow the placement and positioning of a graft within a diseased vessel when the condition or morphology of the vessel prevents use of barbtype attachment means. It would also be advantageous to provide an intraluminal graft structured to be flexible and adjustable to thereby facilitate insertion and placement of the graft within a vessel which displays abnormal morphology.

DISCLOSURE OF THE INVENTION

In accordance with the present invention, an intraluminal vascular graft is structured to be supported within a vessel from a position downstream from, or below, a disease condition existing in the vessel and includes a biocompatible tube supportable within a vessel by adjustable circumferential and longitudinal support structures. The circumferential and longitudinal support structures provide means for supporting the biocompatible tube within the vessel, and further provide means for limiting movement of the intraluminal graft within the vessel. Movement inhibitor structures may further be associated with the longitudinal and/or circumferential support structures to limit movement of the graft tube within the vessel and to enhance attachment of the graft to the vessel. The intraluminal vascular graft may be structured with one or more caudal leg portions positionable within one or two bifurcations extending from the vessel in which the graft is placed. Alternatively, the intraluminal graft may be a single tube having no extending leg portions. The intraluminal vascular graft may be secured to the intima of the vessel by attachment means induced by an inflammatory response between the graft and the inner wall of the vessel. While the intraluminal vascular graft of the invention may be used in any number of various vascular repairs, it is particularly suitable in the repair of aneurysms of the abdominal aorta, which is one of the most common types of aneurysm.

The intraluminal vascular graft includes a tube of biocompatible material, such as Dacron® or polytetrafluoroethylene, which is capable of being compressed to provide a graft having a reduced circumferential dimension to permit insertion of the graft into a vessel (e.g., femoral artery) for transportation to the disease site. The tube is thereafter capable of expanding radially outwardly from a central longitudinal axis to provide a close fit between the tube structure and the inner vessel wall. The tube has at least two open ends- one which may be termed a proximal end, and one which may be termed a distal end. As used herein, "proximal" refers to the end of the graft which is positioned upstream or which is oriented toward the cranium of the patient. As used herein, "distal" refers to the end of the graft which is positioned downstream or which is oriented toward the caudal end of the patient.

When used in vessels which bifurcate, such as the abdominal aorta, the tube may include leg portions which extend into one or more branching vessels resulting from the bifurcation. The tube may have a single leg portion extendable into a single branching vessel. More suitably, however, the tube has two leg portions extendable into both branching vessels. The relative lengths of the two leg portions may be equal, or one may be longer than the other as dictated by the particular condition of the vessel. The leg portions facilitate positioning and support of the device in bifurcated vessels by providing a crotch area between the two leg portions which straddle the crotch between the vessels of the bifurcation.

In an alternative embodiment, the tube may have a single leg portion with a hole formed in the tube opposite the leg portion to allow fluid flow into the other branching vessel. In another alternative embodiment, the tube may have a single leg portion with no corresponding opening in opposing position, or the tube may have a first leg portion and a second, the shorter leg portion having no opening therein to allow blood flow therethrough. An intraluminal vascular graft of such construction would be useful in repairing bifurcated vessels (such as an iliac artery) where the surgeon specifically desires to restrict blood flow to a single branching vessel of the bifurcation.

The tube of the intraluminal vascular graft may also comprise a single tube, having no extending leg portions, which is suitable for repairing less complex vessel structures or disease conditions. In a single tube configuration, the intraluminal vascular graft includes only a proximal opening and a distal opening to allow movement of blood through the graft.

The intraluminal vascular graft further includes expandable circumferential support structures secured at the proximal end of the tube and at the distal end of the tube. The expandable circumferential support structure positioned at the distal end of the graft tube, also referred to herein as the expandable caudal ring, provides a means for positioning the graft tube within the vessel and for supporting the graft within the vessel at a point distal to the disease condition. In bifurcated vessels, the expandable caudal ring is particularly structured to provide support and seating of the graft tube at the point where the vessel bifurcates, or on what is otherwise termed the cusp of the bifurcation.

The expandable circumferential support structures may be constructed of any material, or may take any form, which provides the ability of reducing the circumferential dimension of the circumferential support structures prior to deployment of the intraluminal graft, and which allows the structures to expand once the graft is deployed. The expandable circumferential support structures may be expandable by unrelated means, such as an angioplasty balloon introduced following insertion of the graft, or may be self-expanding, such as a tensioned ring of flexible material which unwinds or decompresses upon release of a compression force.

The intraluminal vascular graft also includes at least two adjustable longitudinal support structures oriented along the length of the biocompatible graft tube and positioned at about sixty to one hundred and twenty degrees to the expandable circumferential support structures. The longitudinal support structures maintain the tube in its full, predetermined length following deployment within the vessel. By "predetermined" is meant that the length of the longitudinal support structures and graft tube which is required to repair the vessel is determined by known x-ray or fluoroscopic techniques, and prior to insertion, the surgeon may modify or adjust the longitudinal support structures and graft tube to fit the vessel. The longitudinal support structures support the graft longitudinally within the vessel and act in tandem with the expandable caudal ring to support the graft in the vessel from the distal end of the graft upward. The longitudinal support structures also maintain the graft in place and function to keep the graft from moving back and forth longitudinally within the vessel.

The longitudinal support structures are most suitably flexible so that they may bend in a direction transverse the longitudinal axis of the graft tube, such as may be necessary when the graft is deployed in a vessel which bends along its course. The longitudinal support structures, in an alternative embodiment, may be further adjustable after the graft is placed within the vessel. Such adjustability may be provided, for example, by use of longitudinal support structures having telescoping members.

The expandable circumferential support structures and the adjustable longitudinal structures generally comprise what may be called the frame of the graft structure. The frame is secured to the biocompatible graft tube by any suitable means, such as tacking, sewing or by weaving the graft tube to the frame. The frame may be positioned within the graft tube material so that the frame is exposed to fluid moving through the graft tube. Alternatively, and more suitably, the frame is disposed on the outer surface of the graft tube material and is, therefore, positioned between the inner vessel wall and the outer surface of the graft tube.

When the frame is disposed on the outside of the graft tube, movement inhibiting structures may be positioned along the longitudinal and circumferential support structures and oriented toward the vessel wall. The movement inhibiting structures may be in the form of scales or graspers oriented in either, but preferably both, directions (cranial or caudal) along the longitudinal axis of the vessel, which impinge against the inner wall of the vessel. The movement inhibiting structures limit longitudinal movement of the graft tube along the length of the vessel which may be caused by eddy currents or other forces in a flowing stream. The movement inhibiting structures may be located at the distal end of the tube, at the proximal end of the tube, along the length of the tube, or any combination of locations. In addition, or alternatively, movement inhibiting structures may be associated with the biocompatible tube. The movement inhibiting structures may penetrate into the media lining the vessel wall (e.g., clotted matter), but do not penetrate through the adventitia.

Fixed attachment of the graft tube to the interior wall, or the intima, of the vessel is provided by inducement of an inflammatory response between the outer surface of the intraluminal vascular graft and the inner wall of the vessel. Thus, the graft tube is caused to attach to the interior wall of the vessel. The inflammatory response is caused by placing along the frame and/or tube structure a material known to cause an inflammatory response in tissues. Such materials known to cause an inflammatory response may include those which are retained permanently in place between the vessel wall and the graft, or those which are absorbed by the body. Materials for inducing an inflammatory response which may be used in the invention include cat gut, nylon and cellulose.

To further attach the intraluminal vascular graft to the vessel, the graft tube material (e.g., Dacron® or PTFE) may be coated or otherwise treated with a material or substance which induces an inflammatory response, such as polylactic acids, polyglycolic acids or polyamino acids. The graft tube may also be constructed or treated in a manner which encourages ingrowth of tissue on to the graft tube to enhance or promote incorporation of the intraluminal graft structure into the surrounding vascular environment. Such treatment may include coating or infusing the graft tube material with collagen. Also, the longitudinal and/or circumferential support structures may be constructed of a material which inherently causes an inflammatory response and/or which is constructed of a material which promotes ingrowth of tissue into the support structure. The longitudinal and/or circumferential support structures may also be treated, such as by coating with collagen, polylactic acids, polyglycolic acids or polyamino acids to promote ingrowth of the device into the surrounding vascular tissue.

Support of the intraluminal vascular graft within the vessel is enhanced by providing leg portions extending from the distal or caudal end of the biocompatible graft tube. The graft tube may preferably include two leg portions positionable within each vessel branching from a main bifurcating vessel (e.g., the iliac arteries). Providing leg portions stabilizes the graft within the main vessel, provides support for the graft structure within the vessel by positioning the crotch between the two leg portions over the crotch spanning between the two bifurcating vessels, and facilitates seating of the frame on the cusp of the bifurcation. The leg portions may also be necessary where the disease (e.g., aneurysm) extends into or along one or both of the branching vessels of the bifurcation. The leg portions may be the same length or may vary in lengths comparatively.

The leg portions of the graft may include longitudinal support structures along the length of the leg portion, and may include expandable ring structures. Further, movement inhibiting structures as described previously may be positioned along the longitudinal or circumferential support structures of the leg portions, or along the length of tubular material of the leg portions, to limit or prevent movement of the leg portions within the branching vessels. Attachment means as previously described may also be associated with the outer surface of either or both leg portions.

The intraluminal vascular graft is suitable for use in vascular repairs where a very short, or no, length of unaffected vessel exists between the beginning point of disease in a vessel and the location of vessels branching from the affected vessel. For example, in a significant number of patients, the abdominal aortic aneurysm occurs just below the renal arteries which branch from the abdominal aorta, and as a result, very little unaffected aorta exists just below the renal arteries. That area of unaffected vessel just below the renal arteries may be termed, for the sake of this disclosure, the "neck" of the vessel.

In such situations as just described, the limited existence of a neck of the vessel makes it impossible or unlikely to attach a vascular graft thereto by the conventional means of hooks or barbs. Therefore, the present invention allows positioning of the intraluminal vascular graft within the vessel and maintenance of the graft in place by virtue of the fact that it is supported at the distal end thereof and supported upwardly, eliminating the need for attachment by hooks or barbs. The present invention also allows deployment of the graft at the point of branching of any other vessels (e.g., renal arteries) without occlusion of the branching vessels. In an embodiment suitable for the described condition, two or more of the longitudinal support structures may extend beyond the proximal end of the graft tube material and be positionable against the inner wall of the vessel beyond the area of branching vessels (e.g., renal arteries) to facilitate positioning of the graft tube around the branching vessels; but neither the extending longitudinal support structures nor the tube occlude the branching vessels. The extension of the frame allows the graft to be well-centered in the vessel if a turn or kink exists in the vessel to be repaired.

The intraluminal graft is delivered to the site of the diseased vessel by transport means which are sized and structured to contain the intraluminal graft therein or thereabout, and which facilitate insertion of the device through the arterial system. A particularly suitable transport means comprises a capsule within which the intraluminal graft is retained in a collapsed condition, and deployment means for releasing the intraluminal graft from the capsule and positioning it within the vessel.

The capsule is structured to navigate smoothly through the tortuous pathway that can often be encountered in the arterial tree. The capsule and associated deployment structures, described hereafter, are inserted into a small incision made in an artery or vein located remotely from the area of diseased vessel. With respect to aortic aneurysms, for example, the capsule is inserted into a femoral artery and passed upwardly to the abdominal aorta. A guide wire may be used initially to determine proper placement. The capsule containing the graft may then be threaded about or over the guide wire to the point of deployment.

When the capsule has reached the disease site, a deployment structure deploys the device within the vessel. Expansion actuator means may be included, such as an angioplasty balloon, to facilitate expansion of the device. Alternatively, the deployment structure may be structured with expansion actuator means to both deploy and facilitate expansion of the graft. Exemplar deployment means include a hydraulic force.

In a first suitable implantation method, the capsule containing the collapsed graft is inserted into the diseased vessel. A guide wire may be used to insert the capsule. Once positioned at the site of deployment, deployment means urge the intraluminal vascular graft from inside the capsule by, for example, pushing the graft out of a hole formed in the end of the capsule. The capsule is then retrieved from inside the body. Alternatively, the capsule may be removed from about the graft structure, such as when the capsule is in the form of a tear-away sheath. The graft may be assisted in deployment from the capsule by means of a stabilizer rod which is manipulable from outside the patient's body.

An angioplasty balloon may be used to assist in deploying and expanding the graft. Alternatively, the graft may be deployed from the capsule by application of a hydraulic force provided by infusion of saline solution. Once the graft is released from the capsule, the compressive forces which kept the frame of the graft positioned within the capsule are released and the graft expands outwardly from a central axis of the graft. The capsule and other deployment structures are retrieved from inside the vessel by withdrawing those structures over the inserted guide wire. Use of hydraulic means to deploy the graft reduces the amount of deployment structures required for deployment, and insertion is possible through a smaller incision.

When deployed in a vessel, the expandable circumferential support structures may spring open to expand the graft tube within the vessel. The expansion of the graft tube may be full or partial, depending upon the configuration of the support structures and/or the material from which they are constructed. Expansion may be assisted with additional expansion means, such as a balloon catheter or a hydraulic force applied to the inner area of the graft tube.

The longitudinal support structures maintain the graft in an elongated expansion within the vessel. The expandable caudal ring and the longitudinal structures maintain the graft in position within the vessel at the distal or caudal end of the vessel. When deployed in a bifurcating vessel, like the abdominal aorta, the expandable caudal ring comes to rest upon the cusp of the bifurcation to support the graft. The longitudinal support structures are forced radially outwardly from a central axis of the graft by force of the expandable caudal ring, and the longitudinal support structures aid in expansion of the graft.

After the graft has been deployed and extended radially outwardly to fit the vessel, attachment means which may be associated with the device contact the inner wall of the vessel and immediately an inflammatory response is initiated. Attachment of the graft to the vessel wall may be completed within a few days to weeks after insertion of the graft. While the inflammatory response continues and the vascular graft becomes more attached to the vessel wall, the frame structure of the graft keeps the graft in place and fully supported within the vessel.

When the graft tube is structured with leg portions, the leg portions are deployed in generally the same manner as described previously. If one leg portion is used, that leg portion is typically deployed within the iliac artery through which the deployment structures are passed. When two leg portions are used, the deployment of the second leg may be accomplished in different ways. For example, the second leg portion, when structured without longitudinal supports, may be folded up against the outer surface of the graft prior to deployment. With proper positioning of the graft, the second leg portion will naturally extend into the appropriate vessel bifurcation.

In alternative deployment means, a catheter or guide wire may be inserted into the other femoral artery (which was not used for insertion of the vascular graft) prior to insertion of the device into the femoral artery. The guide wire or catheter may be inserted until the distal end (the end inserted into the vessel) reaches the point of bifurcation. The distal end can then be passed across the bifurcation and down through the other artery (through which deployment of the device will take place) until the distal end of the guide wire or catheter can be retrieved from the other artery to outside the patient's body. The distal end of the guide wire or catheter may then be sutured to the leg portion of the device which will ultimately be positioned in the other iliac artery. The entire intraluminal vascular graft is then inserted into the femoral artery and through the iliac artery until positioned within the aorta. Following deployment of the entire graft tube within the aorta, the guide wire, catheter or suture attached to the second leg portion is retrieved from the other femoral artery. As a result, the second leg is brought over to the other iliac artery and into position. The guide wire, catheter or suture is then removed from the other artery.

In an alternative procedure, the guide wire or catheter passed through the other femoral artery may be passed across the bifurcation and manipulated until the distal end of the guide wire or catheter encounters the second leg portion of the graft tube. The distal end of the guide wire or catheter may be configured with a hook or other similar device for attaching the second leg portion thereto. Once the second leg portion is engaged by the distal tip, the guide wire or catheter may be retrieved from the vessel thereby causing the second leg portion to be brought over to the other branching vessel. The guide wire or catheter may then be removed from the artery.

BRIEF DESCRIPTION OF THE DRAWINGS

In the drawings, which illustrate what is currently considered to be the best mode for carrying out the invention.

DETAILED DESCRIPTION OF THE DRAWINGS

Figure 1:
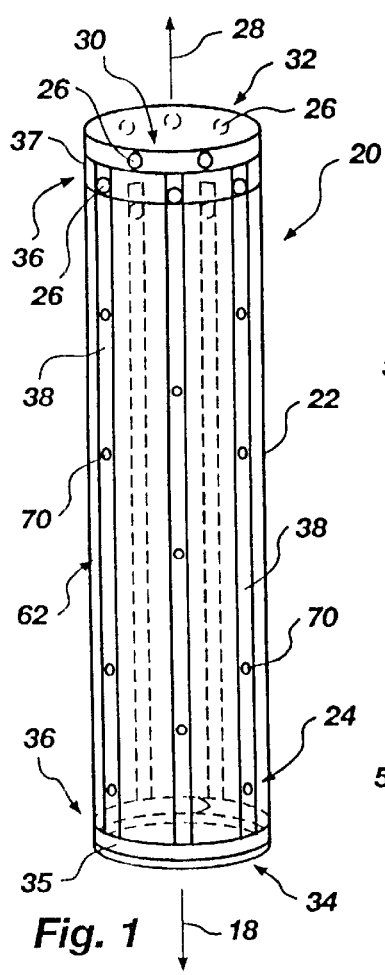
FIG. 1 is a view in elevation of a first embodiment of the intraluminal vascular graft.

FIG. 1 illustrates a simplified version of the intraluminal vascular graft 20 which generally comprises a tubular body 22 and a frame 24. Attachment means 26 are also illustrated. The tubular body 22 is made from a biocompatible material which has the ability to be manipulated into a tube of smaller circumferential dimension relative to a longitudinal axis 28 formed through the tubular body 22. The ability to be manipulated to a circumferentially smaller dimension allows the tubular body 22 to be positioned within a transportation means sized to fit within a vessel lumen. The tubular body 22 is open at either end, providing a passageway 30 for fluid therethrough. One end of the tubular body 22 may be denoted as the proximal or cranial end 32, and the opposite end thereto may be denoted the distal or caudal end 34.

The frame 24 of the intraluminal vascular graft 20 generally comprises circumferential support structures 36 which provide support of the caudal end 34 of the vascular graft 20 and provide expansion to the tubular body 22 upon deployment, and a plurality of longitudinal support structures 38 extending along the length of the tubular body 22 for supporting the tubular body 22 in a fully extended state upon deployment. The circumferential support structures 36 and longitudinal support structures 38, in tandem, function to provide support to the vascular graft 20 from the distal end 34 upward.

The circumferential support structures 36 have a determined maximum circumferential dimension when deployed in the vessel. The circumferential support structures 36 are made in any configuration, or of any material, which renders the structures capable of being manipulated to present a smaller circumferential dimension relative to the longitudinal axis 28. The configuration or material of the support structures 36 should also render the circumferential support structures 36 capable of expanding radially outward from the longitudinal axis 28 to a circumferential dimension approaching the determined maximum when the vascular graft 20 is deployed. The circumferential support structures 36 include an expandable caudal ring 35 and an expandable cranial ring 37.

Figure 2:
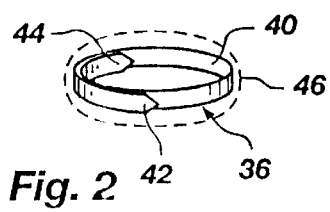
FIG. 2 is a view in elevation of an exemplar circumferential support structure in a compressed state.
Figure 3:
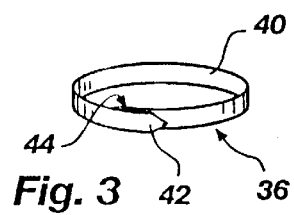
FIG. 3 is a view in elevation of the circumferential support structure shown in FIG. 2 in an uncompressed state.

Exemplar circumferential support structure 36 configurations are illustrated in FIGS. 2–5. In FIG. 2, a circumferential support structure 36 is illustrated as a flexible ring 40 having a first end 42 and a second end 44. The ring 40 is made of a material which allows the ring 40 to be compressed, as shown in FIG. 2, to present a smaller circumferential dimension 46. When the compressive force is released, the ring 40 expands again to its maximum circumferential dimension, as illustrated in FIG. 3. The flexible ring 40 may be made of such materials as spring metal, plastic and rubber.

Figure 4:
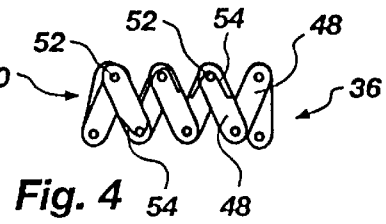
FIG. 4 is a view in elevation of an alternative embodiment of the circumferential support structure in a compressed state.
Figure 5:
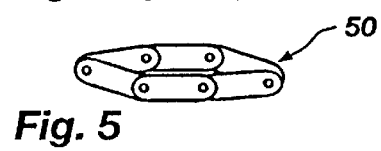
FIG. 5 is a view in elevation of the circumferential support structure shown in FIG. 4 in an expanded state.

In an alternative embodiment shown in FIG. 4, a circumferential support structure 36 may be formed from a plurality of links 48 pivotally attached at either end to adjacent links 48 to form a ring 50. The links 48 are articulable about pivot points 52 which allow the links 48 to be compressed together in side-by-side formation as shown in FIG. 4. Spring pins 54 may be positioned about the pivot points and biased between adjacent links 48 to provide an automatic self-expanding capability to the ring 50 when the compressive force is released. A flattened ring 50 results when the compressive force is removed, as shown in FIG. 5.

Figure 6:
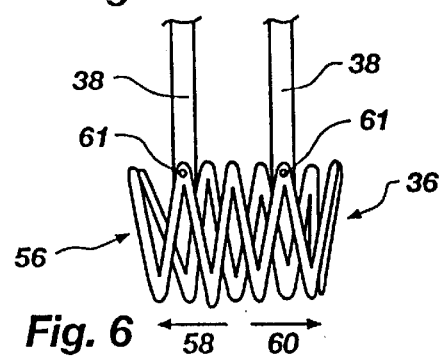
FIG. 6 is a view in elevation of another alternative embodiment of the circumferential support structure.

In yet another embodiment of a circumferential support structure 36, a ring 56 of flexible material which is formed of lengths extending in opposing directions, generally in a zig-zag or sine wave configuration, is compressible to a smaller circumferential dimension as shown in FIG. 6. However, when the compression force is removed the ring 56 springs outwardly, in the direction of arrows 58 and 60, to a maximum circumference. The expandable caudal ring 35 and the expandable cranial ring 37 may be constructed or configured in any manner previously described or in a manner which provides the requisite compressibility and expandability. The expandable caudal ring 35 may be of the same type, construction or configuration as the expandable cranial ring 37, or they may differ.

FIG. 6 also illustrates a means by which the longitudinal support structures 38 may be attached to the circumferential support structures 36 and be deployed therewith. As illustrated, the longitudinal support structures 38 may be secured to the ring 56 in a manner which allows the longitudinal support structures 38 to articulate with and move relative to the ring 56. Such means may be pivot pins 62, as shown. Although illustrated in FIG. 6 as being connected to one circumferential support structure 36, the longitudinal support structures 38 may be connected to both the cranial ring 37 and caudal ring 35 as described.

Figure 8:
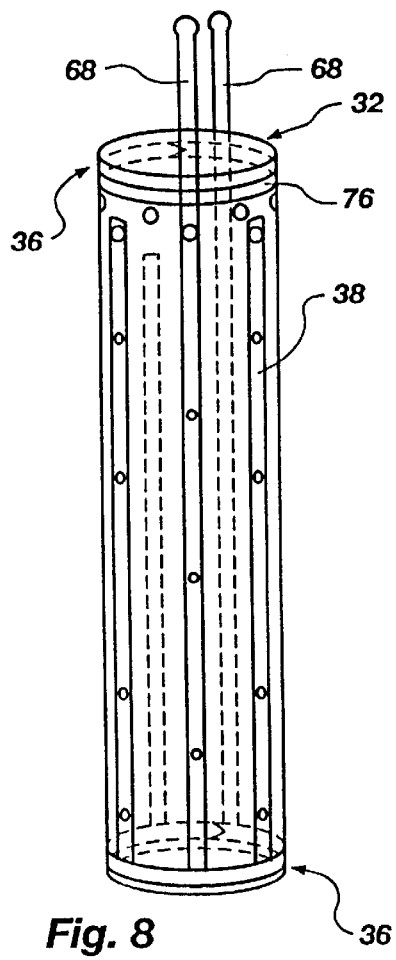
FIG. 8 is a view in elevation of another alternative embodiment of the vascular graft illustrating extended longitudinal support structures.

The longitudinal support structures 38 of the frame 24 extend along the length of the tubular body 22 and support the tubular body 22 in a fully extended form when deployed. The longitudinal support structures 38 also serve to limit longitudinal movement of the graft 20 once deployed in the vessel. As shown in FIGS. 1 and 8, the longitudinal support structures 38 may be secured to the circumferential support structures 36 or to the caudal ring 35. However, the longitudinal support structures 38 may be secured directly to the outer surface 62 of the tubular body 22, such as by suturing or by positioning the longitudinal support structures 38 in pockets (not shown) or channels formed on the surface of the tubular body 22, rather than being secured to the circumferential support structures 36. Attachment of the longitudinal support structures 38 to the expandable circumferential support structures 36 may more readily facilitate deployment and positioning of the longitudinal support structures 38, however.

The frame 24 is shown in the drawings as being positioned on an outer surface 62 of the tubular body 22, such that the frame is positioned between the tubular body 22 and the inner wall of the vessel. However, the frame 24 may be positioned alternatively within the tubular body 22 so that the frame is exposed to fluid moving through the passageway 30. The frame 24 will be described throughout this disclosure as being positioned on the outside of the tubular body 22, but the disclosed structure and function of the frame 24 is equally applicable, with minor modification, to being positioned within the tubular body 22.

The length of the longitudinal support structures 38 is predetermined by the surgeon prior to the vascular graft 20 being inserted into the patient. A measurement of the area and length of the vascular disease (e.g., aneurysm) is made by means well known in the art, such as by x-ray or fluoroscopic techniques. Once the measurement is taken, the proximal end 32 of the vascular graft 20 may be modified by various means to provide the proper length of vascular graft 20 for implantation. For example, the tubular body 22 and the longitudinal support structures 38 may be trimmed by the surgeon to the correct length.

Figure 7:
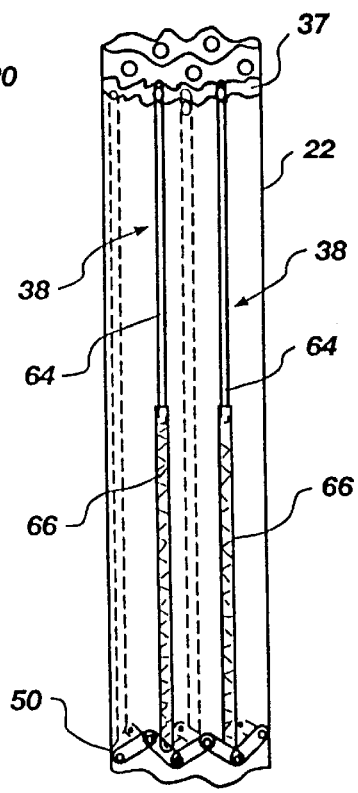
FIG. 7 is a view in elevation of an alternative embodiment of the vascular graft illustrating an alternative embodiment of the longitudinal support structures.

Alternatively, the longitudinal support structures 38 may be adjustable in length to modify the length of the vascular graft 20. Correspondingly, the tubular body 22 is constructed, such as with an extra length of material, to be adjustable with the longitudinal support structures. An example of means for adjusting the longitudinal support structures 38 is illustrated in FIG. 7 where the longitudinal support structures 38 are shown comprising a first support member 64 and a second support member 66 telescopically positioned relative to each other. Thus, once deployed in the diseased vessel, the length of the longitudinal support structures 38 may be modified to provide an optimal fit within the vessel.

The longitudinal support structures 38 are made of a suitable material, or of an appropriate construction, to provide flexibility of the longitudinal support structures 38. Flexibility of the structures 38 not only aids in deploying the vascular graft 20, but assists in insertion of the device when fed into a tortuous arterial system, or when deployed in a vessel which, as a matter of course, has a significant bend therein.

In cases, as previously described, where the area of healthy vessel is shortened near branching vessels, making attachment of the vascular graft 20 difficult, it may be desirable to provide at least two longitudinal support structures 68 which extend beyond the proximal end 32 of the tubular body 22, as shown in FIG. 8. The extended longitudinal support structures 68, when the device is properly deployed, extend above the point of attachment of the device to the wall of the vessel and extend above the branching vessels. However, the extending longitudinal support structures 68 do not occlude, obstruct or otherwise interfere with the branching vessels.

Figure 9:
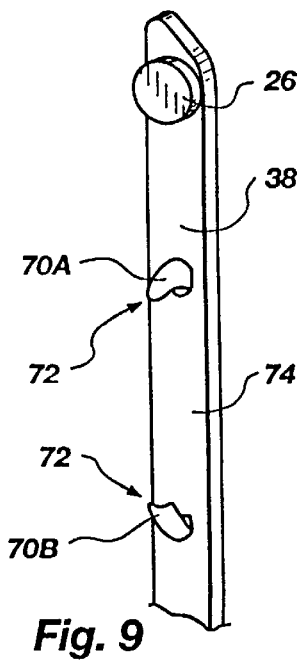
FIG. 9 is an enlarged perspective view of a longitudinal support structure illustrating positioning of attachment means and grasping means thereto.

When the longitudinal support structures 38 are positioned on the outside of the tubular body 22, as shown in FIG. 1, the structures 38 may be constructed with movement inhibiting structures 70 oriented outwardly from the vascular graft 20 and toward the inner wall of the vessel (not shown). The movement inhibiting structures 70, which, for example, may take the form of a plurality of scales, as shown more clearly in FIG. 9, is configured with an engaging edge 72 which engages the wall of the vessel. The scales engage the vessel wall and limit back and forth movement (longitudinal movement) of the vascular graft 20 once deployed. The movement inhibiting structures 70 or scales may be oriented cranially, as shown at 70B in FIG. 9. Alternatively, the scales may be oriented caudally, as shown at 70A. The movement inhibiting structures 70 may also be a mixture of cranially- and caudally-oriented structures. The movement inhibiting structures 70 may be located only at either end 32, 34 of the vascular graft 20, or may be located along the length of the vascular graft 20 as suggested in FIG. 1, or may be located in both locations.

The vascular graft 20 is supported within the vessel by the circumferential and longitudinal support structures as previously described, and attachment of the vascular graft 20 to the inner wall of the vessel is accomplished in the present invention by expansion of the circumferential support structures against the inner vessel wall and by engagement of the movement inhibiting structures with the vessel wall. Attachment of the vascular graft 20 also may be accomplished by providing a means or material which initiates an inflammatory response in the vessel intima or inner wall. By such attachment means 26, the vessel is caused to attach to the vascular graft 20. The attachment means 26 may be any suitable device or material which is known to cause an inflammatory response. Exemplar materials include cat gut, cellulose and nylon. Thus, as more clearly seen in FIG. 9, the attachment means 26, for example, may be a three-dimensional formation of cellulose attached to the outer surface 74 of the longitudinal support structures 38. Alternatively, or in addition, attachment means 26 may also be formed on the material of the tubular body 22 near the proximal end 32 thereof. Alternatively, the longitudinal and/or circumferential support structures may be constructed of a material, or may be coated with a material, which induces an inflammatory response. Such materials may include polylactic acids, polyglycolic acids or polyamino acids. Similarly, the tubular body 22 may be coated or otherwise treated with such materials.

At a minimum, it is desirable to provide attachment means 26 at the distal end 34 of the vascular graft 20 to provide attachment of the device to the vessel proximate the area of support of the structure on the cusp of a bifurcation. It is also desirable, however, to provide attachment means 26 near or at the proximal end 32 of the vascular graft 20 at the beginning and above the diseased portion of the vessel. It may also be desirable to provide attachment means 26 along the length of the vascular graft 20 or in either or both leg portions of the tubular graft 20, as described further below.

Figures 10, 11:
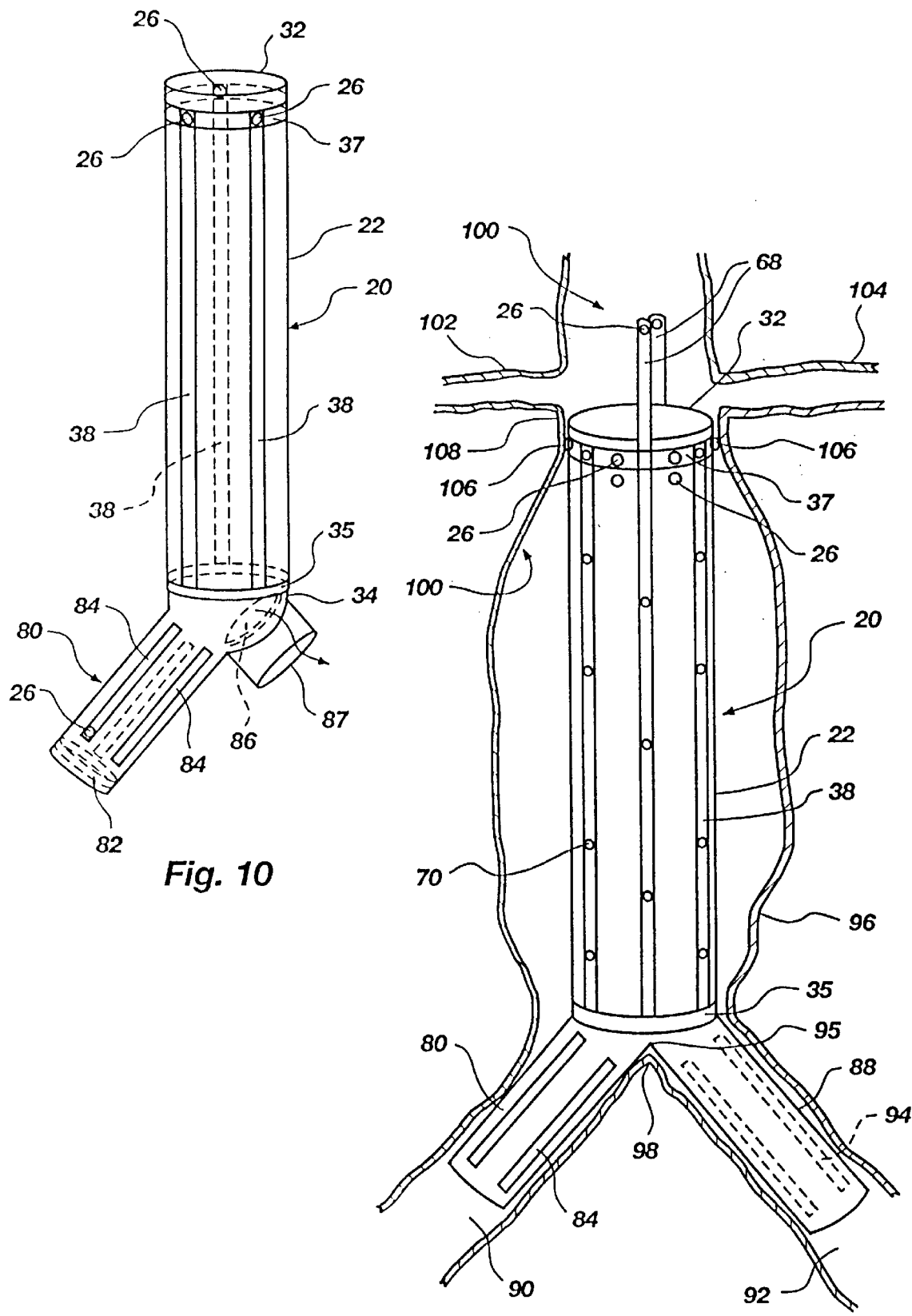
FIG. 10 is a view in elevation of another alternative embodiment of the vascular graft illustrating the inclusion of a single leg portion.
FIG. 11 is a view in elevation of another alternative embodiment of the vascular graft, having two leg portions, positioned within an abdominal aorta and bifurcating iliac arteries.

The tubular body 22 may, in one embodiment, comprise a single, relatively straight tube of material, as shown in FIGS. 1, 7 and 8. A single tube configuration is suitable for repairing vessels which do not have branching vessels therefrom. Alternatively, however, the tubular body 22 is constructed with one or more leg portions to enhance support of the graft 20 on the cusp of a bifurcated vessel. As shown in FIG. 10, the tubular body 22 may include a leg portion 80 which is positionable in a vessel which bifurcates or branches from the main diseased vessel. The leg portion 80 may include a circumferential support structure 82 positioned at the end of the leg portion opposite the expandable caudal ring 35. In addition, or alternatively, a plurality of longitudinal support structures 84 may extend along the length of the leg portion 80. Attachment means 26 may also be associated with the leg portion 80 as described previously herein.

When the alternative embodiment of the device shown in FIG. 10 is deployed in a bifurcated vessel, such as the abdominal aorta, a hole 86 (shown in phantom) may be provided near the distal end 34 of the tubular graft 22 to allow fluid to flow into the other branching vessel. Preferably, when deployed in the abdominal aorta, a short leg portion 87 is provided to extend a short distance into the other branching vessel to assure positioning of the graft 20 in the vessel and to facilitate support of the graft 20 on the cusp of the bifurcation. When deployed in other bifurcating vessels, such as an iliac artery, it may be desirable, in response to a particular disease condition, to block flow of blood to one of the branching vessels. Therefore, deployment of a graft as shown in FIG. 10 would be appropriate, but no hole 86 would be provided, thereby blocking flow to the other branching vessel.

In a preferred embodiment, as shown in FIG. 11, the graft 20 includes a first leg portion 80 and a second leg portion 88, each of which is sized to be positionable within branching or bifurcating vessels such as the right iliac artery 90 and the left iliac artery 92 depicted. The second leg portion 88 may include longitudinal support structures 94, as suggested in phantom in FIG. 11, or a circumferential support structure (not shown) may be associated with the second leg portion 88. Attachment means as previously described may also be associated with the second leg portion 88 to help anchor it to the vessel wall. Alternatively, no support structures or attachment means need be associated with the second leg portion 88.

The embodiment of the intraluminal vascular graft 20 shown in FIG. 11 is preferred for repair of vessels, such as the abdominal aorta 96, which bifurcate since the two leg portions 80, 88 provide a crotch 95 between the leg portions 80, 88 which seats on the crotch 98 of the bifurcated vessel 96. Thus, the graft 20 is stably supported within the vessel, or aorta 96, by positioning of the circumferential support structures 36, the longitudinal support structures 38 and the leg portions 80, 88 spanning the crotch 98 of the vessel. The graft 20 is thereby supported in position while the attachment means 26 induce attachment of the graft 20 to the vessel wall 100.

The placement of the vascular graft 20 within the diseased vessel, here shown as the abdominal aorta 96, is illustrated in FIG. 11. When deployed in a bifurcating vessel like the abdominal aorta, the expandable caudal ring 35 is seated upon and supported by the bifurcation of the vessel, otherwise referred to as the crotch 98 of the bifurcation. The longitudinal support structures 38 extend the length of the tubular body 22 and support the vascular graft in position within the vessel 96. Two extending longitudinal support structures 68A and 68B extend above the proximal end 32 of the tubular body 22 and are positioned against the inner wall 100 of the vessel. The extending longitudinal support structures 68A, 68B are positioned above the renal arteries 102, 104 and away from the openings to the renal arteries 102, 104 so as to not obstruct those branching vessels. The extending longitudinal support structures 68A, 68B may have attachment means 26 associated therewith for initiating an inflammatory response with the inner wall 100 of the vessel.

The proximal end 32 of the tubular body 22 extends to just below the renal arteries 102, 104. An inflammatory response 106, and thus an attachment, is illustrated, for example, between the inner wall 100 of the vessel and the attachment means 26 positioned on the longitudinal support structures 38, or expandable cranial ring 37 or tubular body 22. The attachment by inflammatory response occurs at the neck 108 portion of the vessel. Once pressure on the vessel 96 is relieved by directing the blood through the vascular graft 20, the vessel wall 100 will tend toward the tubular body 22, and may be engaged by the movement inhibiting structures 70. In embodiments where the tubular body 22 is, or the longitudinal and/or circumferential support structures are, formed from, or are treated with, material which induces an inflammatory response, the vessel wall 100 may tend to adhere to the vascular graft 20 and thus to incorporate it into the vessel 96.

The first leg portion 80 and second leg portion 88 are each positioned within one of the iliac arteries which bifurcate from the aorta 96. The leg portions 80, 88 may be maintained in position and in full extension by longitudinal support structures 84, 94 positioned relative to the leg portions 80,88. However, no support structures may be needed or desired.

Figure 12:
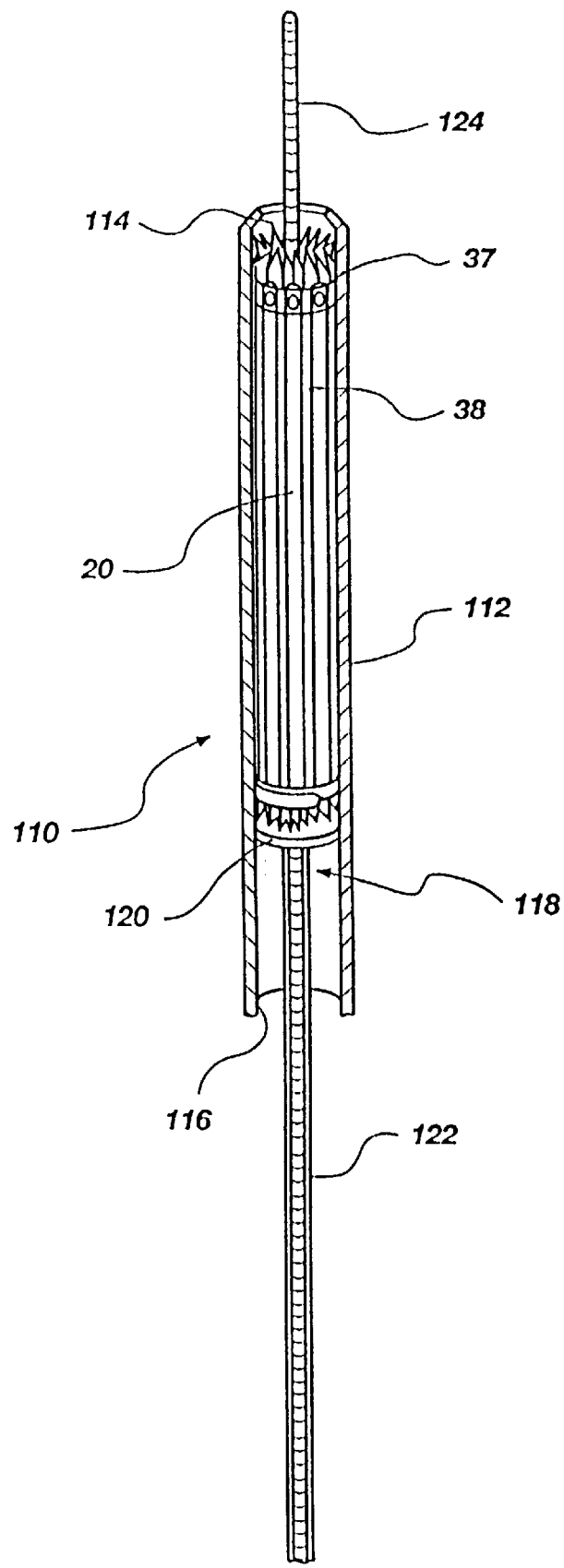
FIG. 12 is a view in cross section of a transporting and deployment structure for positioning the vascular graft into a vessel.

Deployment of the vascular graft 20 may be accomplished in a variety of ways. Generally, however, transportation structure may be used to retain the vascular graft 20 in a pre-deployment state and to move the vascular graft 20 through the arterial system to the area of deployment. An exemplar structure for transporting and deploying the vascular graft is shown in FIG. 12. The transportation structure 110 includes a capsule 112 configured and sized to receive and retain the vascular graft 20 in a circumferentially compressed state, compressed along its length in a plane or direction transverse the longitudinal axis 126 of the vascular graft 20 in a non-longitudinally lengthening manner such that the plane of the vascular graft 20 remains the same from an expanded state to a compressed state, as shown.

The capsule 112 may be formed as a solid tube of flexible material which allows the capsule 112 to bend while being passed through the sometimes tortuous arterial system. The capsule 112 may alternatively be formed from a continuous coil of material which imparts flexibility to the structure. Alternatively, the capsule 112 may be in the form of a tear-away sheath which is removable from about the vascular graft 20 once the graft is in position within the vessel.

The capsule has 112 an open proximal end 114 and an open distal end 116, and the vascular graft 20 is positionable within the capsule 112 in a circumferentially compressed state as shown. A stabilizer rod 118 is positioned at the distal end 116 of the capsule 112 and is positioned adjacent the distal end of the vascular graft 20. The stabilizer rod 118 may generally comprise a platform 120 and pusher rod 122, and is structured to allow the placement of a guide wire 124 through the capsule 112 and through the compressed vascular graft 20 as shown. The guide wire 124 facilitates placement of the vascular graft 20 in the vessel and may be positionable relative to the graft 20 and capsule 112 in any appropriate manner.

Figure 13D:
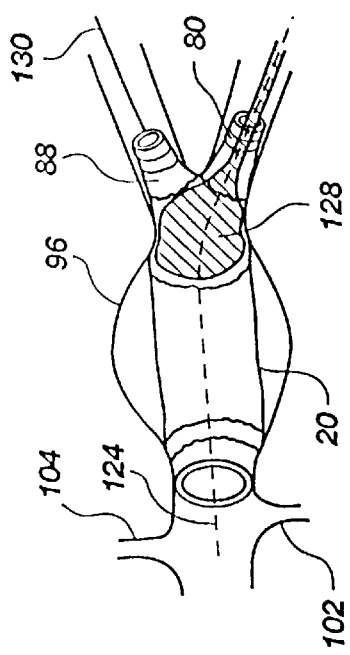
FIG. 13a–f illustrates deployment of a vascular graft within a diseased vessel.
Figure 13E:
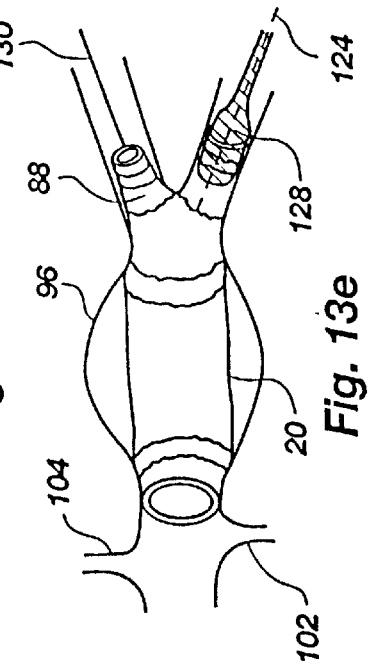
Figure 13F:
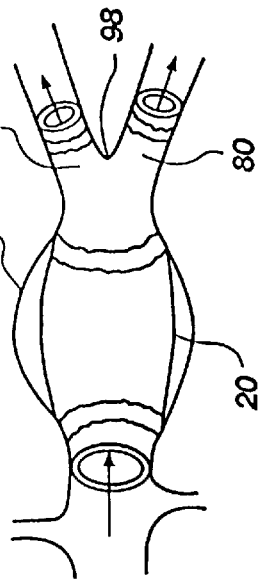
Figure 13A:
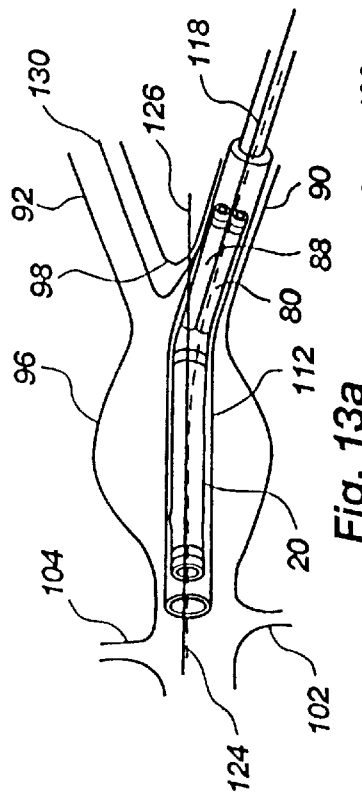
Figure 13B:
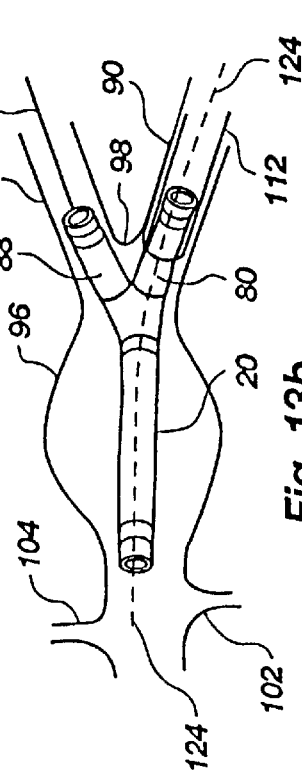

The stabilizer rod 118 may preferably be constructed with a hollow tube, such as the pusher rod 122, so that fluid substances may be passed therethrough into the vessel, as described further below. Once the vascular graft 20 is correctly positioned within the vessel 96, the stabilizer rod 118 maintains the vascular graft 20 in place while the capsule 112 is withdrawn from about the graft 20, as shown in FIGS. 13a and 13b. When a tear-sheath is used as the capsule 112, a line or similar means may be used to initiate tearing of the sheath and the sheath may be withdrawn from the artery.

Upon removal of the capsule 112 from around the vascular graft 20, the compressive force provided by the capsule 112 to keep the vascular graft 20 compressed is removed. As a result, the circumferential support structures 36 are allowed to expand and the vascular graft 20 will expand radially outward from a central longitudinal axis 126. Expansion of the vascular graft 20 may be aided by various means.

Figure 13C:
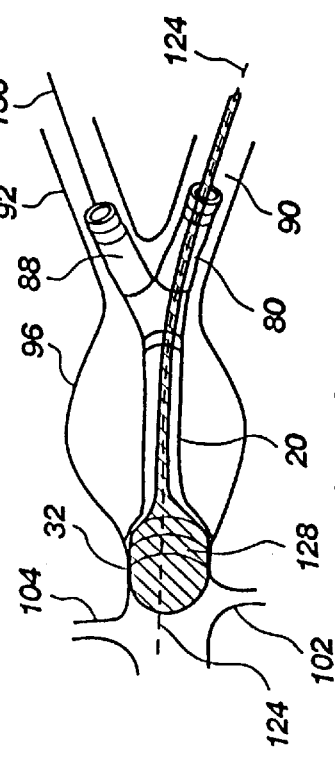

For example, as shown in FIG. 13c, a balloon catheter 128 may be introduced into the femoral artery (not shown), then into the right iliac artery 90 and through the vascular graft 20 after the stabilizer rod 118 has been retrieved from within the vascular graft 20. Placement of the balloon catheter 128 may be facilitated by the guide wire 124 which remains positioned within the vascular graft 20. The balloon catheter 128 is positioned at the proximal end 32 of the vascular graft 20 and fluid, such as air or saline, is introduced into the balloon 128. Expansion of the balloon 128 forces the vascular graft 20 outwardly to the maximum circumferential limit of the circumferential support structures 36. As the balloon 128 is withdrawn from inside the vascular graft 20, the expanded balloon 128 sequentially expands the more distal regions of the vascular graft 20 until the vascular graft 20 is fully expanded, as shown in FIGS. 13c, 13d and 13e. The balloon catheter 128 is then retrieved through the iliac artery 90. The guide wire 124 is also removed.

Alternative expansion means may comprise introducing a hydraulic force into the vascular graft 20. For example, a bolus of saline solution may be introduced into the inside of the vascular graft 20 by way of the hollow pusher rod 122 of the stabilizer rod 118. The hydraulic force provided by the saline facilitates outward expansion of the vascular graft 20.

The procedure for positioning, deploying and expanding the vascular graft 20 within the vessel 96 described hereinabove is appropriate for positioning single tubular grafts, as illustrated in FIG. 1, and for positioning tubular grafts having a single leg portion which is positioned within the iliac artery through which the device is transported. However, when the device includes either a shortened leg portion, as shown in FIG. 10, or two leg portions, as shown in FIG. 11, additional procedures must be performed to bring the second leg portion over from the iliac artery through which the device is transported so that the second leg portion may be positioned within the other branching vessel.

A first method for positioning the second leg portion 88 into the other iliac artery 92 is illustrated in FIGS. 13a–13f where a catheter or guide wire 130 is inserted into the femoral artery which is not used for transport of the device to the vessel 96, here illustrated as the left femoral artery. The guide wire 130 is inserted in the arterial system prior to insertion of the intraluminal vascular graft 20 into the arterial system. The guide wire 130 is directed through the left iliac artery 92 to the point of bifurcation of the vessel 96. The guide wire 130 is then passed over the crotch 98 and is directed through the right iliac artery 90 through which the device will ultimately be transported.

The guide wire 130 is passed out of an incision formed through the right femoral artery (not shown) through which the intraluminal vascular graft will be positioned. The end of the guide wire 130 is sutured to the second leg portion 88, or otherwise attached in a manner which may be easily broken or severed when necessary. The capsule 112 containing the vascular graft 20 is then inserted into the right femoral artery and iliac artery 90 as described previously above.

While the stabilizer rod 118 is still in place maintaining the vascular graft 20 in position within the vessel 96, the guide wire 130 is withdrawn from the left iliac artery 92 thereby bringing the second leg portion 88 over the crotch 98 and into the left iliac artery 92. At this point, expansion means may be introduced into the left femoral and iliac arterial route to provide expansion of the second leg portion 88. Once positioned and expanded, the guide wire 130 is detached from the second leg portion 88 and the guide wire 130 is removed from the arterial system. Alternatively, a long suture line which is previously secured to the second leg portion in the manner previously described may be detached from the second leg portion 88, and the suture line removed from the left femoral artery.

Figure 14:
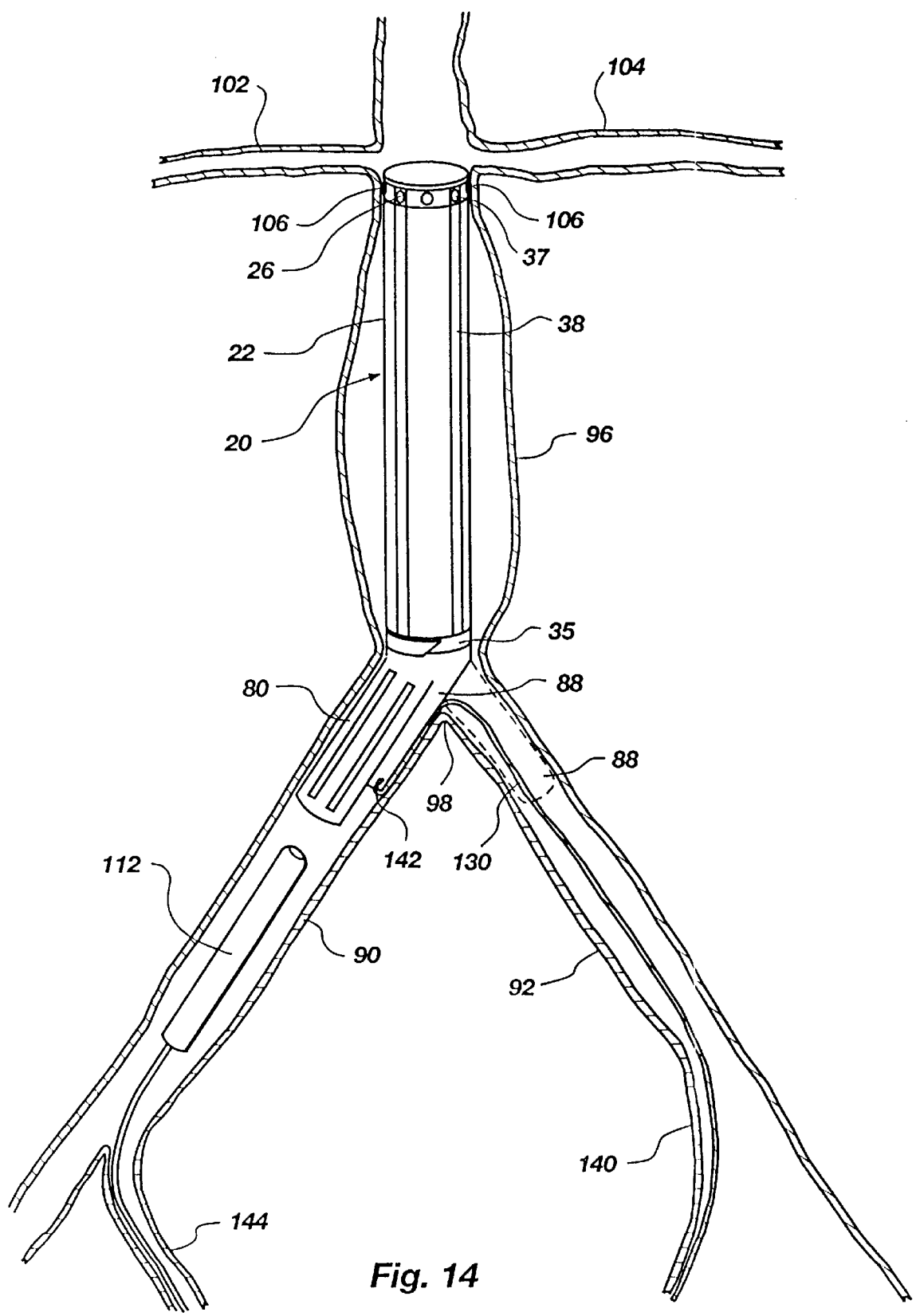
FIG. 14 illustrates an alternative implantation procedure for a vascular graft embodied with two leg portions.

Alternatively, as illustrated in FIG. 14, the vascular graft 20 may be deployed in the vessel 96 first, as described previously, and then the guide wire 130 is introduced into the left femoral artery 140 and left iliac artery 92. The guide wire 130 is advanced through the left iliac artery 92 to the crotch 98 of the bifurcation 98. The guide wire 130 is urged across the crotch 98 and down the right iliac artery 90. The guide wire 130 is formed with a hook 142 or other device capable of grasping the second leg portion 88. The second leg portion 88 is secured by the hook 142 and the guide wire 130 is withdrawn, urging the second leg portion 88 over the crotch 98 and into the left iliac artery 92, as shown in phantom in FIG. 14. The hook 142 of the guide wire 130 is thereafter disengaged from the second leg portion 88 and the guide wire 130 is removed from the left iliac artery 92 and left femoral artery 140. Expansion means may thereafter be introduced into the right femoral artery 144 and right iliac artery 90 as previously described.

Alternatively to the foregoing deployment procedures, the second leg portion 88 may be deployed in the left iliac artery 92 by compressing the second leg portion 88 against the tubular body 22 in the area of the expandable caudal ring 35, and as the capsule 112 is removed from about the vascular graft 20, and the caudal ring 35 expands, the second leg portion 88 moves independently into the left iliac artery 92. This deployment method may be particularly suitable in an embodiment where the second leg portion 88 is shortened.

The intraluminal vascular graft disclosed herein may be used in the repair of any diseased vessel, including but not limited to the repair of aneurysms and partial or full stenoses or blockages. The vascular graft may be deployed in any vessel, whether straight or bifurcated. The concept may be adapted to virtually any type or configuration of vascular repair in either humans or other animals. The structure of the invention may be modified to meet the demands of the particular application. Hence, reference herein to specific details of the illustrated embodiments is by way of example and not by way of limitation. It will be apparent to those skilled in the art that many additions, deletions and modifications to the illustrated embodiments of the invention may be made without departing from the spirit and scope of the invention as defined by the following claims.

What is claimed is:

1. An intraluminal vascular graft structure for maintaining and repairing diseased or damaged vessels in animals comprising:
   a flexible tubular body formed from a biocompatible material, said tubular body having an open proximal end for orientation upstream in a vessel, an open distal end for orientation downstream in said vessel and a longitudinal axis oriented between said open ends, said tubular body being inwardly compressible along the entirety of its length in a direction transverse said longitudinal axis and in a longitudinally non-lengthening manner to provide compression of said tubular body to a first reduced cross section and subsequent radially-outward expansion of said tubular body to a second expanded cross section;
   frame structure positioned to contact said tubular body with a portion of said frame structure oriented substantially in alignment with said longitudinal axis and with a portion positioned to extend around the circumferential dimension of said tubular body, said frame structure being formed and shaped to support said flexible tubular body circumferentially at said distal end and to rigidly support said flexible tubular body longitudinally from said distal end to said proximal end.

2. The intraluminal vascular graft structure of claim 1 wherein said frame structure comprises at least one circumferential support structure substantially oriented about the circumference of said distal end and longitudinal support structures oriented substantially in alignment with said longitudinal axis, said longitudinal support structures being interconnected with said circumferential support structure at said distal end.

3. The intraluminal vascular graft structure of claim 2 wherein said flexible tubular body further includes two leg portions extending from said distal end, said leg portions forming a crotch area therebetween to provide support of said frame structure at said crotch area.

4. Intraluminal vascular graft structure comprising:
   a tubular body constructed of a biocompatible material and having a proximal end and a distal end sized and formed to be positioned on the cusp of a bifurcated vessel and to be supported on said cusp, said tubular body being structured to be inwardly compressible in a direction transverse a longitudinal axis and in a longitudinally non-lengthening manner for deployment and subsequent radially-outward expansion;
   at least one leg portion attached to said tubular body and extending from said distal end;
   frame structure attached to said tubular body and configured to support said tubular body in a circumferentially expanded mode at said distal end of said tubular body and to rigidly support said tubular body longitudinally from said distal end to said proximal end; and
   non-perforating attachment structure positioned proximate said tubular body in proximity to said proximal end to provide attachment of said tubular body to the inner wall of a vessel.

5. The intraluminal vascular graft of claim 4 wherein said frame structure further comprises circumferential support structures which are compressible to provide a reduced cross sectional dimension and which are expandable again to provide a selected maximum cross sectional dimension, said circumferential support structures being positioned at said proximal end and said distal end of said tubular body.

6. The intraluminal vascular graft of claim 5 wherein said frame structure further includes a plurality of longitudinal support structures interconnected with said circumferential support structures and extending along a length of said tubular body between said proximal end and said distal end to provide rigid longitudinal support to said tubular body.

7. The intraluminal vascular graft of claim 6 further including movement inhibiting structures positioned in logitudinal alignment along said frame for engaging said inner wall of said vessel.

8. The intraluminal vascular graft of claim 6, wherein said plurality of longitudinal support structures includes at least two longitudinal support structures which extend beyond said proximal end of said tubular body.

9. The intraluminal vascular graft of claim 4 wherein said tubular body further includes an opening formed in said distal end of said tubular body proximate said leg portion.

10. The intraluminal vascular graft of claim 4, wherein said at least one said leg portion has associated therewith a support structure.

11. The intraluminal vascular graft of claim 4 wherein said frame structure is at least partially constructed from material which induces an inflammatory response in vascular tissue to promote attachment of said vascular tissue to said frame structure.

12. The intraluminal vascular graft of claim 4 wherein said frame structure is treated with a substance which facilitates ingrowth of tissue into said frame for incorporation of said frame into said vessel.

13. The intraluminal vascular graft of claim 4 wherein said tubular body is treated with a substance which facilitates ingrowth of tissue into said frame for incorporation of said frame into said vessel.

14. The intraluminal vascular graft of claim 4 further including transportation structure sized to receive and retain said tubular body, frame and attachment means therein for transport to a vessel for deployment.

15. The intraluminal vascular graft of claim 14 wherein said transportation structure includes a capsule sized to receive said tubular body and deployment structure for maintaining said tubular in position within said vessel while said capsule is removed from said vessel.

16. The intraluminal vascular graft of claim 15 further including guide wire structure to facilitate placement of said tubular body.

17. An intraluminal vascular graft structure for maintaining and repairing diseased or damaged vessels in animals comprising:
   a flexible tubular body formed from a biocompatible material, said tubular body having an open proximal end, an open distal end, a selected length between said open ends and a longitudinal axis between said open ends, said tubular body being inwardly compressible in a non-longitudinally lengthening manner along the entirety of its length in a direction transverse said longitudinal axis from an expanded cross sectional dimension to a radially inwardly reduced cross sectional dimension;
   frame structure positioned adjacent said flexible tubular body, said frame structure including a circumferential support structure attached to said flexible tubular body at said distal end thereof sized and configured to be supported on the cusp of a bifurcated vessel and longitudinal support structures in substantial alignment with said longitudinal axis of said flexible tubular body, said longitudinal support structures being positioned relative to said circumferential support structure to extend coextensively with said length of said flexible tubular body to support said flexible tubular body from said distal end to said proximal end;
   non-perforating attachment structure positioned proximate said tubular body at said proximal end thereof to attach said flexible tubular body to the tissue of the inner wall of the vessel in which said flexible tubular body is positioned.

18. The intraluminal vascular graft structure of claim 17 wherein said circumferential support structure is constructed to be compressible to a reduced circumferential dimension and expandable to a selected maximum circumferential dimension.

19. The intraluminal vascular graft structure of claim 18 wherein said frame structure is positioned within said tubular body.

20. The intraluminal vascular graft structure of claim 18 wherein said frame structure is positioned outside said tubular body.

21. The intraluminal vascular graft structure of claim 20 wherein said non-perforating attachment structures are portions of material positioned on said longitudinal support structures, said portions of material producing an inflammatory response on the interior wall of a vessel to provide a non-puncturing attachment of said vascular graft structure to said wall of a vessel.

22. The intraluminal vascular graft structure of claim 21 further including movement inhibiting structures formed proximate said longitudinal support structures and oriented toward said vessel wall for engaging said vessel wall.

23. The intraluminal vascular graft structure of claim 21 wherein said tubular body further includes a first leg portion extending from said distal end thereof.

24. An intraluminal vascular graft structure for maintaining and repairing diseased or damaged vessels in animals comprising:
   a flexible tubular body formed from a biocompatible material, said tubular body having an open proximal end for orientation upstream in a vessel, an open distal end for orientation downstream in said vessel and sized and shaped for positioning at the cusp of a bifurcation of a vessel and a longitudinal axis oriented between said open ends, said tubular body being inwardly compressible in a direction transverse said longitudinal axis for providing expansion from a first reduced cross section about said longitudinal axis to a second radially expanded cross section from said longitudinal axis;
   frame structure positioned to contact said tubular body with a portion oriented substantially in alignment with said longitudinal axis and with a portion positioned to extend around the circumferential dimension of said tubular body, said frame structure being formed and shaped to support said flexible tubular body circumferentially at said distal end and to rigidly support said flexible tubular body longitudinally from said distal end to said proximal end.

25. An intraluminal vascular graft structure for maintaining and repairing diseased or damaged vessels in animals comprising:
   a flexible tubular body formed from a biocompatible material, said tubular body having an open proximal end for orientation upstream in a vessel, an open distal end for orientation downstream in said vessel and a longitudinal axis oriented between said open ends, said tubular body being inwardly compressible in a direction transverse said longitudinal axis for providing expansion from a reduced cross section to a radially expanded cross section;
   frame structure positioned in contact with said tubular body and having a portion oriented substantially in alignment with said longitudinal axis and also having a portion positioned to extend around the circumference of said tubular body, said frame structure being formed and shaped to support said flexible tubular body circumferentially at said distal end and to rigidly support said flexible tubular body longitudinally from said distal end to said proximal end; and
   attachment structures positioned in proximity to said frame structure to promote attachment to the tissue of a vessel wall, said attachment structures being formed of a material configured to create an inflammatory response with said vessel wall by frictional and non-perforating contact with said vessel wall to facilitate integration of said attachment structures into said vessel wall.

26. The intraluminal vascular graft structure of claim 25 wherein said attachment structures are formed of a non-perforating material.

27. The intraluminal vascular graft structure of claim 26 wherein said attachment structures comprise a flat band of material that has a first end and a second end, wherein said band is movable between a first expanded position wherein said first end overlaps said second end to provide a first circumference selected to urge said vascular graft outward against the vessel wall and a second position wherein said first end is moved about said flat band to have a second circumference less than the circumference of said vessel.

28. The intraluminal vascular graft structure of claim 27 wherein said first end is formed and shaped to snuggly contact said flat band and to slide over the wall of said vessel.

29. An intraluminal vascular graft structure for maintaining and repairing diseased or damaged vessels in animals comprising:

a flexible tubular body formed from a biocompatible material, said flexible tubular body having an open proximal end, a cylindrical portion extending therefrom and a Y-shaped portion extending from said cylindrical portion, said Y-shaped portion having a first leg and a second leg defining a crotch configured for support by the cusp of a bifurcation in a vessel;

frame structure comprising a circumferential support structure attached to said cylindrical portion proximate said crotch, said circumferential support being sized and shaped to extend substantially about the circumference of said cylindrical support and to be supported by the vessel at said cusp, and longitudinal support structures attached to said circumferential support structure in substantial alignment with the longitudinal axis of said flexible tubular body and being coextensive with said flexible tubular body to support said flexible tubular body from said circumferential support structure outwardly.

30. Intraluminal vascular graft structure comprising:

a tubular body constructed of a biocompatible material and having a proximal end and a distal end sized and formed to be positioned on the cusp of a bifurcated vessel and to be supported on said cusp;

two leg portions attached to said tubular body and extending from said distal end;

frame structure attached to said tubular body and configured to support said tubular body in a circumferentially expanded mode at said distal end of said tubular body and to rigidly support said tubular body longitudinally from said distal end to said proximal end; and non-perforating attachment structure positioned proximate said tubular body in proximity to said proximal end to provide attachment of said tubular body to the inner wall of a vessel.

31. The intraluminal vascular graft of claim 30 wherein one of said two leg portions is open to allow fluid flow therethrough and one of said two leg portions is closed to prevent fluid flow therethrough.

32. The intraluminal vascular graft of claim 30 wherein one of said leg portions is shorter in length dimension than the other.

33. An intraluminal vascular graft structure for maintaining and repairing diseased or damaged vessels in animals comprising:

a flexible tubular body formed from a biocompatible material, said tubular body having an open proximal end, an open distal end, a selected length between said open ends and a longitudinal axis between said open ends and having a first leg portion and a second leg portion, said tubular body being inwardly compressible along the entirety of its length in a plane transverse said longitudinal axis from an expanded cross sectional dimension to a radially inwardly reduced cross sectional dimension;

frame structure positioned adjacent to and on the outside of said flexible tubular body, said frame structure including a circumferential support structure attached to said flexible tubular body at said distal end thereof sized and configured to be supported on the cusp of a bifurcated vessel and said circumferential support being constructed to be compressible to a reduced circumferential dimension and expandable to a selected maximum circumferential dimension longitudinal support structures in substantial alignment with said longitudinal axis of said flexible tubular body, said longitudinal support structures being positioned relative to said circumferential support structure to extend coextensively with said length of said flexible tubular body to support said flexible tubular body from said distal end to said proximal end;

non-perforating attachment structure formed as portions of material positioned on said longitudinal support structures, said portions of material producing an inflammatory response on the interior wall of a vessel to provide a non-puncturing attachment of said vascular graft structure to said wall of a vessel.

* * * * *